United States Patent [19]
Sinofsky et al.

[11] Patent Number: 6,071,302
[45] Date of Patent: Jun. 6, 2000

[54] PHOTOTHERAPEUTIC APPARATUS FOR WIDE-ANGLE DIFFUSION

[75] Inventors: Edward L. Sinofsky, Dennis; Lincoln S. Baxter, Centerville, both of Mass.

[73] Assignee: Cardiofocus, Inc., West Yarmouth, Mass.

[21] Appl. No.: 09/001,682

[22] Filed: Dec. 31, 1997

[51] Int. Cl.[7] .................................................. A61B 17/36
[52] U.S. Cl. .................. 607/88; 606/15; 606/17
[58] Field of Search ................ 606/2, 7, 10, 11, 606/12, 14, 15, 16, 17; 607/88

[56] References Cited

U.S. PATENT DOCUMENTS

| | | | |
|---|---|---|---|
| 4,233,493 | 11/1980 | Nath | 219/354 |
| 4,398,790 | 8/1983 | Righini et al. | 350/96.18 |
| 4,612,938 | 9/1986 | Dietrich et al. | 606/15 |
| 4,693,556 | 9/1987 | McCaughan, Jr. | 350/320 |
| 4,998,930 | 3/1991 | Lundahl | 606/15 |
| 5,133,709 | 7/1992 | Prince | 606/7 |
| 5,151,096 | 9/1992 | Khoury | 606/7 |
| 5,196,005 | 3/1993 | Dotron et al. | 606/7 |
| 5,415,655 | 5/1995 | Fuller et al. | 606/17 |
| 5,429,635 | 7/1995 | Purcell, Jr. et al. | 606/17 |
| 5,431,647 | 7/1995 | Purcell, Jr. et al. | 606/15 |

FOREIGN PATENT DOCUMENTS

| | | | |
|---|---|---|---|
| 96/07451 | 3/1996 | WIPO | A61N 5/06 |

*Primary Examiner*—Linda C. M. Dvorak
*Assistant Examiner*—Sonya Harris-Ogugua
*Attorney, Agent, or Firm*—Thomas J. Engellenner; Paul D. Durkee; Nutter, McClennen & Fish, LLP

[57] ABSTRACT

A low-profile, diffusive tip apparatus adapted for insertion into a body to deliver phototherapeutic radiation by scattering light in a substantially omnidirectional pattern includes a light-transmissive housing that is adapted for mounting, at its proximal end, onto a fiber optic cable, and, at its distal end, the housing defines or is joined to a light-transmissive cap having a diameter which is not substantially greater than the diameter of the optical fiber. The light transmissive cap region encloses a chamber or reservoir filled with an optically scattering medium and, preferably, hemispherical in shape with a radius of curvature substantially equal to the radius of the housing.

17 Claims, 3 Drawing Sheets

PHOTOTHERAPEUTIC APPARATUS FOR WIDE-ANGLE DIFFUSION

BACKGROUND OF THE INVENTION

The technical field of this invention is phototherapy and, in particular, methods and devices employing optical fibers or other flexible light waveguides to deliver radiation to targeted biological sites.

Fiber-optic phototherapy is an increasingly popular modality for the diagnosis and/or treatment of a wide variety of diseases. For example, in surgery, infrared laser radiation is often delivered to a surgical site by an optically transmissive fiber in order to coagulate blood vessels or cauterize tissue. Similar fiber-optic delivery systems have been proposed for endoscopic or catheter-based instruments to deliver therapeutic radiation to a body lumen or cavity. U.S. Pat. No. 4,878,492 to Sinofsky teaches the use of infrared light to fuse fissures in the endothelial lining of a blood vessel during balloon angioplasty. U.S. Pat. No. 5,053,033 to Clarke teaches the use of ultraviolet light to prevent the proliferation of smooth muscle cells at an angioplasty site.

Fiber-optic irradiation has also been used to activate remote chemical agents with a patient's body. It is well known that light can promote photochemical reactions which, in the absence of light, would proceed either very slowly or not at all. The use of light to activate chemical agents within a patient is often referred to as "photodynamic therapy." For example, U.S. Pat. No. 4,336,809 (Clark) and U.S. Reissue Pat. No. RE 34,544 (Spears) disclose that hematoporphyrin dyes and the like selectively accumulate in tumorous tissue and that cancerous tissue that has taken up the dye can be preferentially destroyed by radiation (typically high intensity red light) absorbed by the dye molecules during phototherapy.

It has also been desirable to promote photothermal treatment for a variety of diseases. This involves the delivery of optical energy to the desired site and the conversion of that optical energy into thermal energy. The intense heat thus generated can cause undesired tissue to undergo necrosis or to separate from a substrate layer. In addition, high energy, rapidly pulsed laser radiation has also been proposed for essentially non-thermal ablation of tissue.

Typically, light can be delivered to the site of the desired phototherapeutic reaction by inserting a fiber-optic cable into a patient and maneuvering it to the site of the desired reaction site. It is often convenient to do so by passing the cable through a body lumen or by passing it directly into a body cavity. The position of the fiber optic cable inside the patient can be monitored by viewing it endoscopically.

In many phototherapeutic applications, it is desirable to uniformly illuminate a large region of tissue inside the patient. The highly-directional distribution of light exiting the fiber-optic cable is ill-suited for such applications. Additionally, the highly directional beam exiting a fiber-optic cable creates a risk of tissue damage by forming hot spots in the illuminated tissue. What is necessary and desirable in the field of phototherapy is an apparatus for the delivery of light having a uniform illumination field over a wide angle to the site of the desired phototherapeutic reaction. A particularly desirable uniform illumination field is one which is uniform over a sphere enclosing the phototherapeutic light source.

Both U.S. Pat. No. 4,693,556 to McCaughan Jr. and U.S. Pat. No. 5,429,635 to Purcell teach the creation of a uniform illumination field substantially as specified above by mounting a globular cap filled with a scattering medium to the tip of a fiber-optic cable having a radius smaller than the radius of the globular cap. Light entering this globular cap is as likely to be scattered backward in the direction of the fiber-optic cable as it is to be scattered forward. Since the globular cap extends radially well beyond the fiber-optic cable on which it is mounted, light scattered in the backward direction can continue to travel in the backward direction unimpeded by the presence of the fiber-optic cable.

Although the conventional globular cap can deliver the required illumination field, its unwieldy shape greatly hampers its usefulness in phototherapy. Because the diameter of the globular cap is so much greater than that of the housing on which it is mounted, it protrudes well beyond the walls of the housing. As a result, the globular cap tends to snag on the incision as it enters or exits the patient. This can result in damage to the diffusive tip assembly.

In addition, because the size of the globular cap is so awkward to maneuver, the surgeon may find it impossible to pass it through constricted spaces within the patient. As a result, the surgeon may find it necessary to reach the phototherapy site by a more circuitous path. This further increases the risk that the globular cap will snag on tissue as the surgeon maneuvers it through the patient. Where the phototherapy site is itself inside a constricted space, the size of the globular cap may make it altogether impossible to reach that site.

It is apparent that in order to scatter light in the backward direction, the conventional globular cap must extend well beyond the wall of the housing on which it is mounted. However the foregoing constraint practically ensures that the conventional globular cap will be extremely awkward to maneuver inside the patient.

Accordingly, it is an object of the invention to provide a diffusive tip apparatus for the delivery of an isotropic and omnidirectional illumination field to a phototherapy site without the danger of snagging tissue within the patient. Such a diffusive tip assembly can scatter light in the backward direction without the need to provide globular cap extending well beyond the wall of the housing on which it is mounted.

SUMMARY OF THE INVENTION

A diffusive tip apparatus according to the invention includes a light transmissive cap forming a cavity containing a light scattering medium within it. The apparatus is adapted to omnidirectionally radiate light into a body cavity while simultaneously retaining a shape optimized for ease of insertion into a patient, for ease of maneuverability within the patient, and for ease of removal from the patient.

As used herein the term "omnidirectional radiation" is intended to encompass the radiation of light in a radiation field having substantially uniform intensity over at least $2\pi$ steradians, and preferably over at least $3\pi$ steradians. The terms "uniform intensity" and/or "substantially uniform intensity" as used herein are intended to describe radiation patterns in which the intensity radiated in any particular direction does not vary more than ±30 percent from the average intensity.

In the preferred embodiment, a distribution of scattered light which is uniform and nearly spherical can be achieved with a "low-profile" diffusive tip assembly. As used herein the term "low-profile" is intended to encompass diffusers wherein the outer diameter of the diffuser housing is no more than 20 percent greater than the outer diameter of the optical fiber (with its buffer intact) and preferably no more than 10 percent greater than the outer fiber buffer diameter. The apparatus of the invention attains this result by using a housing extending along a longitudinal axis and having a light-transmissive housing wall. At its proximal end, the housing is adapted to receive a fiber-optic cable. At its distal end, the housing defines a cap region having a light-transmissive cap wall which encloses a chamber or reservoir filled with a light scattering medium.

Light scattered by the light scattering particles can be deflected in a distal direction, in which case it exits the diffusive tip apparatus by passing through the light-transmissive cap wall. This light forms the forward, or distal, portion of the radiation field. Alternatively, light scattered by the light scattering particles can be deflected in a proximal direction, in which case it exits the diffusive tip apparatus by passing through the light-transmissive housing wall. This light forms the backward, or proximal, portion of the radiation field.

For ease of insertion into and removal from the patient, the wall of the light transmissive cap at the distal end of the housing is substantially flush with the wall of the housing. As used herein, the term "substantially flush" is intended to include an obtuse angle between the housing wall and the cap wall which is greater than 170 degrees. The resulting low profile facilitates passage of the diffusive tip assembly through an incision and movement of the assembly within the patient. In one preferred embodiment, the light-transmissive cap is a hemisphere having a radius of curvature substantially equal to the radius of the housing (e.g., with a radius of curvature within twenty percent of the radius of the housing). However, it is apparent that the cap can be, for example, parabolic, conical, or frustoconical without departing from the scope of the invention. What is desirable in order to maintain a low profile is that the cap have a major axis which is equal to the diameter of the housing or that the cross sectional area of the cap not be substantially greater (i.e., not more than 20 percent greater) than the cross sectional area of the housing.

The light scattering medium can be an optically transmissive medium having light scattering particles suspended within it. Examples of optically transmissive media suitable for use in the cavity formed inside the light transmissive cap include silicone epoxy, deuterium oxide, or water. Examples of light scattering particles suitable for suspension in the optically transmissive medium include silica, alumina, and titania.

BRIEF DESCRIPTION OF THE DRAWINGS

These and other features, aspects and advantages of the invention will be better understood with reference to the following description, the appended claims, and the accompanying drawings in which:

DETAILED DESCRIPTION OF THE ILLUSTRATED EMBODIMENTS

Figure 1:
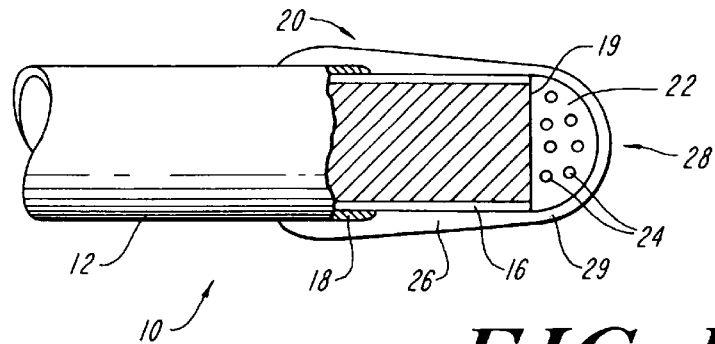
FIG. 1 shows a diffusive tip assembly in accordance with this invention.

Referring to FIG. 1, a diffusive tip assembly 10 according to the invention includes an optical fiber 12 having a fiber-optic core 14, a cladding layer 16 circumferentially disposed around the core 14, and an outer buffer coating 18 circumferentially disposed around the cladding layer 16. The fiber-optic core 14 extends into the proximal end of a housing 20 and terminates in an end face 19.

The housing 20 is formed by a light-transmissive housing wall 26 which defines a tubular chamber into which the fiber-optic core 14 extends. At its proximal end, the housing 20 is adapted to accept the fiber optic core 14. At its distal end, the housing is forms or is adapted to join a cap region 28.

In one embodiment, fluoropolymer materials, such as Teflon® materials and the like, are disclosed as preferred materials for the housing to inhibit contact-adhesion between the tip assembly and biological tissue during procedures. Most preferably, the Teflon® material is a Teflon® FEP material (a polyperfluoroethylene-propylene copolymer). Other Teflon® materials such as Teflon® PFA (a polytetrafluoroethylene polymer with perfluoroalkoxy side chains) and Teflon® PTFE (polytetrafluoroethylene) also can be useful in certain applications. All of these materials have good light transmissivity properties.

The cap region 28, which can be a integral part of the housing, is defined by a light-transmissive cap wall 29 which defines a hemispherical chamber having a radius of curvature comparable to the radius of the housing 20. As a result, the housing wall 26 and the cap wall 29 are substantially flush with each other where the cap region 28 joins the housing 20. As used herein, "substantially flush" is intended to mean that the obtuse angle between the housing wall 26 and the cap wall 29 where the cap region 28 joins the housing 20 is no less than 170 degrees and is preferably 180 degrees. Alternatively, the proximal portion of the housing 20 and the cap region 28 can be separate elements which are joined as part of the assembly process.

The hemispherical chamber of the cap region 28 is filled with a scattering medium 22 in which are suspended individual scattering particles 24. Preferably, the scattering medium 22 has a greater index of refraction than the light-transmissive housing wall 26 and the light-transmissive cap wall 29.

Figure 3:
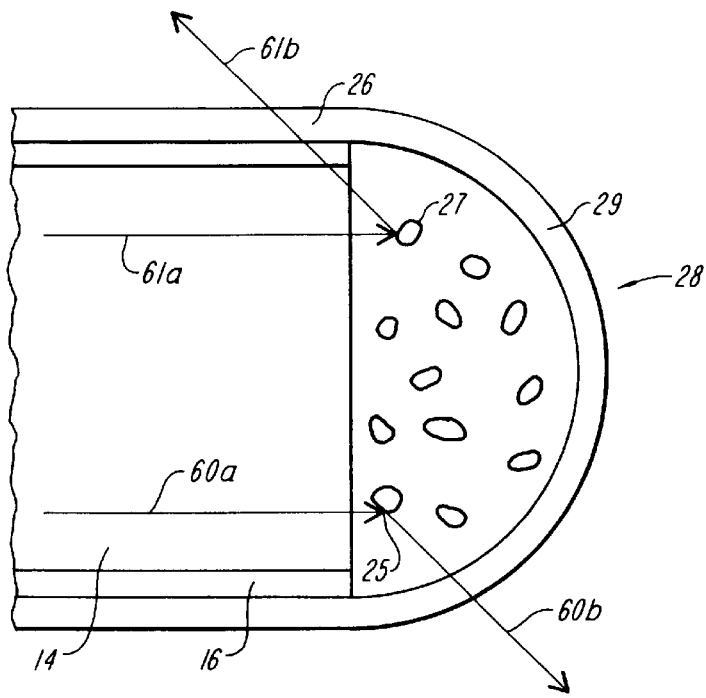
FIG. 3 shows the path traveled by light in the diffusive tip assembly of FIG. 1 to generate the radiation pattern shown in FIG. 2C.

As illustrated in FIG. 3, light propagating through the fiber-optic core 14 enters the scattering medium 22 and scatters off the individual scattering particles 24 before reaching either the housing wall 26 or the cap wall 29. If the scattered light is incident on either the cap wall 29 or the housing wall 26 at an angle exceeding the critical angle for internal reflection for that interface, the light exits the diffusive tip assembly 10.

Figure 2A:
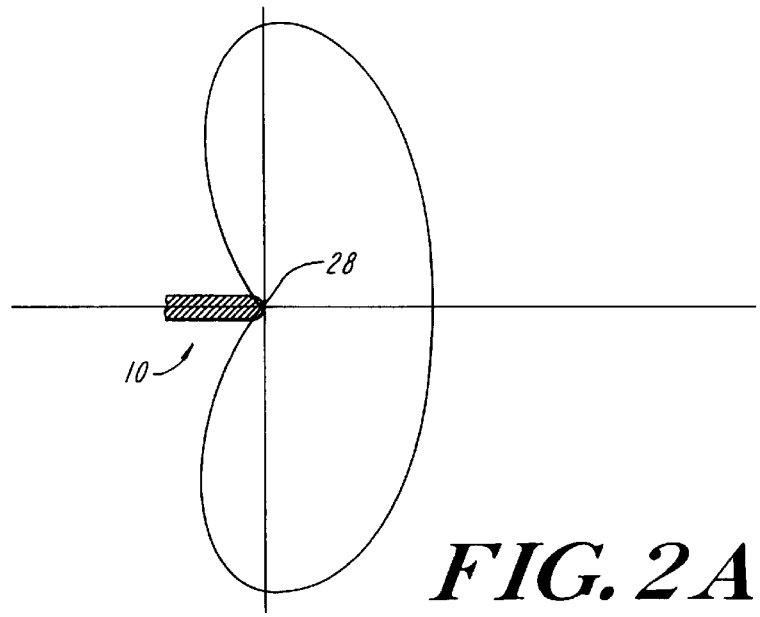
FIG. 2A shows the azimuthal radiation pattern produced by the diffusive tip assembly of FIG. 1 when the concentration of scattering particles is less than optimal.

The radiation pattern formed by light exiting the diffusive tip assembly 10 in the manner set forth above will depend, in part, on the concentration of the scattering particles 24. If the concentration of scattering particles 24 is too high, most of the light will be scattered before reaching the distal tip of the hemispherical cap region 28. This results in a toroidal radiation pattern, an azimuthal cut of which is shown in FIG. 2A, in which most of the optical energy propagating through the scattering medium 22 emerges from the side of the hemispherical cap region 28 and very little reaches the tip.

Figure 2B:
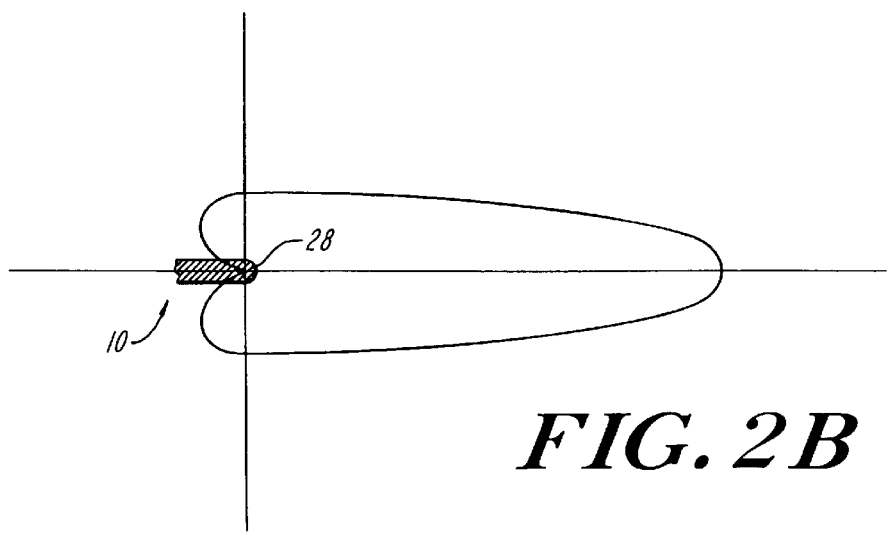
FIG. 2B shows the azimuthal radiation pattern produced by the diffusive tip assembly of FIG. 1 when the concentration of scattering particles is greater than optimal.

Conversely, if the concentration of scattering particles 24 is too low, light propagating through the scattering medium 22 is less likely to encounter a scattering particle 24 and is therefore more likely to exit the hemispherical cap region 28 in its original direction of propagation. The resulting radiation pattern, an azimuthal cut of which is shown in FIG. 2B, shows that most of the optical energy propagating through the scattering medium 22 emerges at the tip and very little emerges from the side.

Figure 2C:
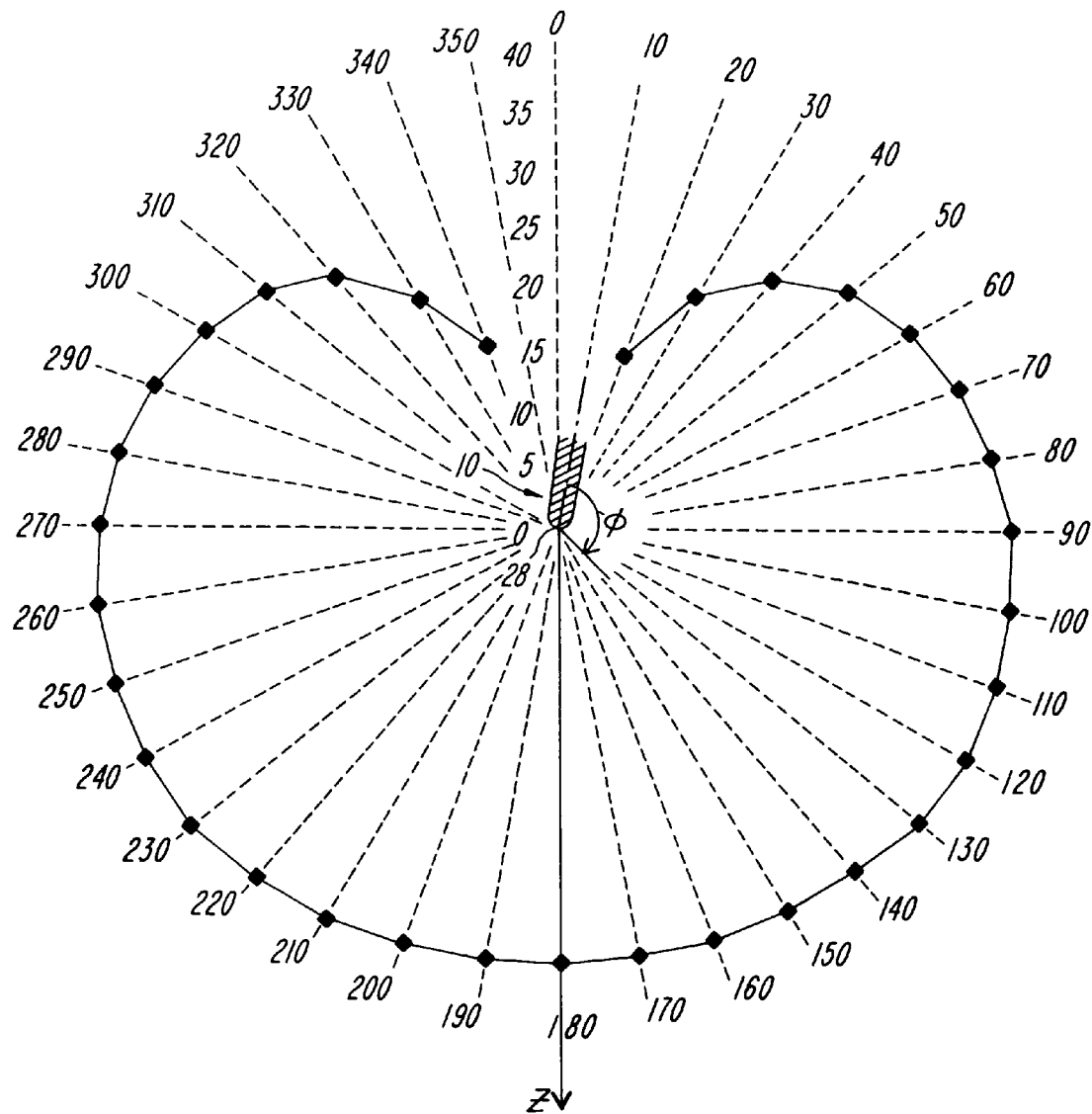
FIG. 2C shows the azimuthal radiation pattern produced by the diffusive tip assembly of FIG. 1 when the concentration of scattering particles is optimal.

FIG. 2C depicts the radiation pattern for a preferred embodiment of the invention in which the scattering concentration is chosen to result in a cardioid pattern which provides a nearly uniform illumination over the $2\pi$ steradian solid angle coincident with the hemispherical cap region 28. For angles outside this range, the magnitude of the radiation pattern decreases slowly with angle until a sharp null is reached along the axis of the fiber optic core 14 in the direction opposite the direction of light propagation in the core. The result is a nearly omnidirectional pattern capable of providing nearly uniform illumination over a solid angle well in excess of $2\pi$ steradians.

The ability of the hemispherical cap region 28 of the invention to radiate in the direction of the fiber-optic cable is best understood with reference to FIG. 3 which shows a first light ray 60a traveling through the fiber-optic core 14 and striking a scattering particle 25 in such a way as to form a scattered ray 60b exiting the light transmissive wall 26 distally. Such a light ray contributes to the radiation pattern in the forward half-plane, namely at azimuth angles $\Phi$ satisfying $90 \leq \Phi < 270$ in FIG. 2C. Similarly, a second light ray 61a traveling through the fiber-optic core 14 can strike a scattering particle 27 in such a way as to form a scattered ray 61b which exits the light transmissive wall 26 proximally. This second light ray 61b, which passes through the transparent fiber-optic core 14 and through the light-transmissive housing wall 26, contributes to the radiation pattern in the backward half-plane in FIG. 2C.

Figure 4:
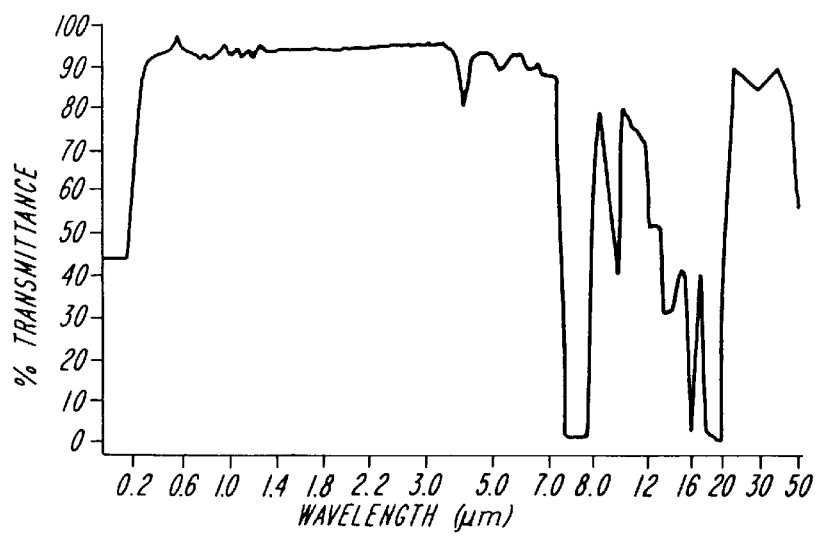
FIG. 4 shows the transmission spectrum of the wall of the hemispherical cap region shown in FIG. 1.

In the preferred embodiment, the diffusive tip assembly shown in FIG. 1 has a Teflon® FEP tubular housing having an outer diameter of about 0.5 millimeters and an inner diameter of about 0.25 millimeters. The transmission spectrum of Teflon® FEP as shown in FIG. 4 indicates that this material is well suited for use as a housing wall for transmitting a broad spectrum of light, from infrared to ultraviolet.

The hemispherical chamber is injected with a scattering medium, such as silicone, epoxy or other polymer. In the preferred embodiment, the chamber is filled with a scattering medium formulated by mixing seventy parts of clear silicone, Mastersil™ formula 151-Clear (available from Masterbond, Inc. of Hackensack, N.J.) with one part of titania filled silicone, Mastersil™ formula 151-White (also available from Masterbond). This results in a diffusive tip assembly which uniformly transmits light at about 633 nanometers. The scattering medium can also be a liquid such as water or a deuterium oxide solution containing colloidal scattering particles such as silica, alumina or titania. In either case, the hemispherical chamber should be completely filled with the scattering medium to avoid entrapment of air bubbles.

The concentration of scattering particles incorporated into the scattering medium can be adjusted to meet particular applications. The following table shows relevant characteristics for three different types of scattering particles. In certain applications, it may desirable to achieve blended characteristics by using more than one type of more scattering particle.

TABLE 1

| Scatterer Characteristics | | |
| --- | --- | --- |
| Scatterer Composition | Density (gram/cc) | Transmission Spectrum ($\lambda$ in mm) |
| $TiO_2$ | 4.0 | .45–11 |
| $SiO_2$ | 2.1 | .2–7 |
| $Al_2O_3$ | 3.6 | .2–9 |

A liquid scattering medium can be used to extend phototherapy into ultraviolet and infrared wavelengths. In particular, deuterium oxide and other heavy water solutions are useful for transmitting infrared light with low losses and minimal heating. Scattering particles suspended in distilled water can be used for extending phototherapy into the ultraviolet.

It will thus be seen that the invention efficiently attains the objects set forth above. Since certain changes may be made in the above construction without departing from the scope of the invention, it is intended that all matter contained in the above description or shown in the accompanying drawings be interpreted as illustrative and not limiting.

It is also to be understood that the following claims are intended to cover all generic and specific features of the invention described herein. When describing the invention, what is claimed as new and secured by Letters Patent is:

1. A low-profile diffusive tip apparatus for diffusion of light propagating through an optical fiber, the diffusive tip apparatus comprising:

a housing extending along a longitudinal axis, the housing having an open proximal end adapted to receive a light-transmitting optical fiber and a closed distal end forming a chamber for containing a scattering material, the distal end having a generally hemispherical shape, at least a portion of the distal end being transparent to light at a desired wavelength for diffusion; and a light scattering material contained within the chamber so as to conform to the hemisperical shape of the housing distal end, the scattering material having a predefined concentration of scattering particles and the shape of the distal end having a predetermined shape, the predefined concentration and the predetermined shape cooperating to provide substantially uniform irradiation over a spherical angle of at least $2\pi$ steradians.

2. The diffusive tip apparatus of claim 1 wherein the housing is tubular and the proximal end further comprises a sleeve portion adapted to slide over the end of a fiber.

3. The diffusive tip apparatus of claim 2, wherein the sleeve portion is further adapted to slide over the end of the fiber which has been stripped of its outer buffer.

4. The diffusive tip apparatus of claim 2, wherein the housing further comprises a polymeric material which can be bonded to the fiber by application of heat following mounting upon the fiber.

5. The diffusive tip apparatus of claim 1 wherein the light scattering material comprises a multiplicity of light scattering particles suspended in an optically transmissive medium.

6. The diffusive tip apparatus of claim 5, wherein the optically transmissive medium is selected from a group consisting of silicone, epoxy, acetic acid, deuterium oxide, water and combinations thereof.

7. The diffusive tip apparatus of claim 5, wherein the scattering particles are selected from a group consisting of silica, alumina, titania and combinations thereof.

8. The diffusive tip apparatus of claim 5, wherein the optically transmissive medium is a heavy water solution.

9. The diffusive tip apparatus of claim 5, wherein the scattering particles are distributed uniformly within the cavity.

10. The diffusive tip apparatus of claim 1 wherein the housing further comprises a fluorocarbon material.

11. The diffusive tip apparatus of claim 10, wherein the housing further comprises a polyperfluoroethylene-propylene copolymer.

12. The diffusive tip apparatus of claim 10, wherein the housing further comprises a polytetrafluoroethylene polymer with perfluoroalkoxy side chains.

13. The diffusive tip apparatus of claim 10, wherein the housing further comprises a polytetrafluoroethylene.

14. The diffusive tip apparatus of claim 1 wherein the scattering material and defined shape of the housing distal end cooperate to yield a pattern of light diffusion over a spherical angle of at least $2\pi$ steradians in which the intensity measured at any point equidistant from the diffusive top apparatus does not vary more than ±30 percent from the average intensity measured at the same distance from the diffuser.

15. The diffusive tip apparatus of claim 1 wherein the distal end of housing is further adapted to provide a substantially flush joint with an optical fiber.

16. A fiber optic instrument for performing phototherapy comprising:

a light transmissive fiber;

a low-profile diffusive tip apparatus for diffusion of light propagating through the light transmissive fiber, the diffusive tip apparatus comprising a housing extending along a longitudinal axis, the housing having an open proximal end adapted to receive the light-transmitting optical fiber and a closed distal end forming a chamber for containing a scattering material, the distal end having a substantially hemispherical shape, at least a portion of the distal end being transparent to light at a desired wavelength for diffusion; and a light scattering material contained within the chamber and conforming to the hemispherical distal end of the housing, the scattering material having a predefined concentration of scattering particles, the predefined concentration and the hemispherical shape cooperating to provide substantially uniform irradiation over a spherical angle of at least $2\pi$ steradians.

17. A method of performing phototherapy within a patient, said method comprising the steps of:

introducing a fiber optic instrument having an optical fiber and a low-profile diffusive tip apparatus for diffusion of light propagating through the optical fiber, the diffusive tip apparatus comprising a housing extending along a longitudinal axis, the housing having an open proximal end adapted to receive a light-transmitting optical fiber and a closed distal end forming a hemispherical chamber for containing a scattering material, at least a portion of the distal end being transparent to light at a desired wavelength for diffusion; and a light scattering material contained within the and conforming to the hemispherical shape of the housing distal end, the scattering material having a sufficient concentration of scatterer particles and the hemispherical shape of the distal tip providing substantially uniform irradiation over a spherical angle of at least $2\pi$ steradians;

positioning the diffusive tip apparatus at a target treatment region within the patient; and activating a light source coupled to the fiber such that light propagates down the fiber and is diffused into the target treatment region to provide phototherapeutic radiation.

* * * * *